US012619997B2

(12) United States Patent
Seamster et al.

(10) Patent No.: US 12,619,997 B2
(45) Date of Patent: May 5, 2026

(54) SYSTEM AND METHOD FOR GENERATING PERSONA DATA OBJECTS USING BIG DATA ANALYTICS

(71) Applicant: Evernorth Strategic Development, Inc., St. Louis, MO (US)

(72) Inventors: Corey Seamster, Riverview, FL (US); Allyson Busch, Orlando, FL (US); Keith R. Melillo, Lake Mary, FL (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 542 days.

(21) Appl. No.: 17/528,803

(22) Filed: Nov. 17, 2021

(65) Prior Publication Data

US 2023/0153837 A1     May 18, 2023

(51) Int. Cl.
| | |
|---|---|
| *G06F 16/00* | (2019.01) |
| *G06F 16/25* | (2019.01) |
| *G06Q 30/0201* | (2023.01) |
| *G16H 10/60* | (2018.01) |

(52) U.S. Cl.
CPC ....... *G06Q 30/0201* (2013.01); *G06F 16/258* (2019.01); *G16H 10/60* (2018.01)

(58) Field of Classification Search
None
See application file for complete search history.

(56) References Cited

U.S. PATENT DOCUMENTS

| | | | | |
|---|---|---|---|---|
| 8,260,635 | B2 * | 9/2012 | Hasan | G16H 50/20 |
| | | | | 705/2 |
| 8,321,239 | B2 * | 11/2012 | Hasan | G16H 50/70 |
| | | | | 705/2 |
| 8,775,242 | B2 | 7/2014 | Tavares | |
| 9,047,611 | B2 * | 6/2015 | Krishnamoorthy | |
| | | | | G06Q 10/1053 |
| 9,372,903 | B1 * | 6/2016 | Richt | G06F 16/254 |
| 9,567,119 | B2 * | 2/2017 | Joplin | B65B 43/52 |
| 9,639,668 | B2 * | 5/2017 | Joplin | B25J 9/0093 |
| 9,779,129 | B1 * | 10/2017 | Lequeux | G06F 16/24 |
| 9,944,419 | B2 * | 4/2018 | Joplin | B65B 35/54 |
| 10,026,048 | B2 | 7/2018 | Leem | |
| 10,331,858 | B2 * | 6/2019 | Miller | G16H 20/13 |
| 10,334,057 | B2 | 6/2019 | Christophe | |
| 10,402,697 | B2 | 9/2019 | Yang | |
| 10,558,554 | B2 | 2/2020 | Bhandarkar | |
| 10,649,983 | B1 * | 5/2020 | Lequeux | G06F 16/24 |

(Continued)

*Primary Examiner* — Jean M Corrielus
(74) *Attorney, Agent, or Firm* — Dickinson Wright PLLC

(57)     ABSTRACT

A method includes receiving at least one input data object corresponding to an individual and determining whether a field of the input data object includes data formatted according to an expected format. The method also includes, storing the data associated with the field of the input data object in the corresponding field of the plurality of fields of the intermediate data object and determining, for the corresponding field of the plurality of fields of the intermediate data object, a classification. The method also includes identifying an aggregated data object having a field having a classification corresponding to the classification of the corresponding of the plurality of fields of the intermediate data object. The method also includes updating a value associated with at least one field of the aggregated data object using the corresponding field of the plurality of fields of the intermediate data object.

20 Claims, 6 Drawing Sheets

(56)  References Cited

U.S. PATENT DOCUMENTS

| | | | | |
|---|---|---|---|---|
| 10,713,287 | B1* | 7/2020 | Rosomoff | G06F 16/332 |
| 10,747,774 | B2 | 8/2020 | Reynolds | |
| 10,896,048 | B1* | 1/2021 | Markson | G16H 70/40 |
| 10,984,900 | B1* | 4/2021 | Bush | G16H 20/10 |
| 11,042,368 | B1* | 6/2021 | Shackelford | G06Q 40/08 |
| 11,056,222 | B1* | 7/2021 | Nambirajan | G06N 5/01 |
| 11,086,757 | B1* | 8/2021 | Ciliberti | G06F 11/366 |
| 11,120,105 | B1* | 9/2021 | Hoffman | G07F 11/1657 |
| 11,126,492 | B1* | 9/2021 | Graklanoff | G06F 11/3048 |
| 11,195,598 | B2* | 12/2021 | Pait | G16Z 99/00 |
| 11,301,483 | B2* | 4/2022 | Canel Lopez | G06F 16/2455 |
| 11,361,381 | B1* | 6/2022 | Lehmuth | G16H 20/10 |
| 11,561,933 | B2* | 1/2023 | Ireifej | G06F 16/258 |
| 12,159,698 | B2* | 12/2024 | Pait | G16H 10/60 |
| 2003/0023607 | A1 | 1/2003 | Phelan | |
| 2006/0173715 | A1* | 8/2006 | Wang | A61B 5/0002 |
| | | | | 600/300 |
| 2007/0168228 | A1* | 7/2007 | Lawless | G06Q 40/08 |
| | | | | 600/300 |
| 2007/0185801 | A1* | 8/2007 | Harrison | G06Q 30/0261 |
| | | | | 705/36 T |
| 2007/0185802 | A1* | 8/2007 | Harrison | G06Q 30/02 |
| | | | | 705/36 T |
| 2007/0185803 | A1* | 8/2007 | Harrison | G06Q 20/387 |
| | | | | 705/36 T |
| 2007/0192431 | A1 | 8/2007 | Liu | |
| 2008/0183495 | A1* | 7/2008 | Butterfield | G16H 10/60 |
| | | | | 715/742 |
| 2009/0012816 | A1* | 1/2009 | Cookson | G16H 40/67 |
| | | | | 705/3 |
| 2010/0070409 | A1* | 3/2010 | Harrison | G06Q 20/10 |
| | | | | 705/39 |
| 2010/0082369 | A1* | 4/2010 | Prenelus | G16H 40/67 |
| | | | | 705/3 |
| 2010/0131299 | A1* | 5/2010 | Hasan | G06Q 10/00 |
| | | | | 705/3 |
| 2010/0211493 | A9* | 8/2010 | Harrison | G07F 7/025 |
| | | | | 705/36 T |
| 2011/0125527 | A1* | 5/2011 | Nair | G16H 50/70 |
| | | | | 705/3 |
| 2011/0125528 | A1* | 5/2011 | Padate | G16H 10/60 |
| | | | | 705/3 |
| 2011/0184958 | A1* | 7/2011 | Krishnamoorthy | G06Q 50/01 |
| | | | | 707/749 |
| 2012/0078664 | A1* | 3/2012 | Hasan | G16H 10/60 |
| | | | | 705/3 |
| 2014/0095698 | A1 | 4/2014 | Grier | |
| 2015/0006201 | A1* | 1/2015 | Pait | G06Q 10/10 |
| | | | | 705/3 |
| 2015/0128532 | A1* | 5/2015 | Miller | G16H 20/13 |
| | | | | 705/2 |
| 2015/0213194 | A1 | 7/2015 | Wolf | |
| 2016/0023787 | A1* | 1/2016 | Joplin | B65B 43/46 |
| | | | | 198/340 |
| 2016/0023790 | A1* | 1/2016 | Joplin | G06Q 10/083 |
| | | | | 198/340 |
| 2016/0026774 | A1* | 1/2016 | Joplin | B65G 1/1378 |
| | | | | 700/216 |
| 2016/0078566 | A1* | 3/2016 | Farrell | G06Q 10/10 |
| | | | | 705/30 |
| 2016/0217161 | A1* | 7/2016 | Haviv | G06F 16/122 |
| 2017/0015005 | A1* | 1/2017 | Joplin | B65B 9/045 |
| 2017/0024541 | A1* | 1/2017 | Joplin | G16H 20/13 |
| 2017/0065485 | A1* | 3/2017 | Trower | B65D 75/54 |
| 2017/0065488 | A1* | 3/2017 | Thach | A61J 7/0454 |
| 2017/0107005 | A1* | 4/2017 | Joplin | G07F 17/0092 |
| 2017/0220768 | A1* | 8/2017 | Tanner, Jr. | G16H 20/13 |
| 2018/0173742 | A1* | 6/2018 | Liu | G06F 16/951 |
| 2018/0225134 | A1* | 8/2018 | Liu | G06F 8/65 |
| 2018/0232497 | A1* | 8/2018 | Hoffman | G16H 20/10 |
| 2019/0156475 | A1* | 5/2019 | Markson | G06T 7/70 |
| 2019/0228847 | A1* | 7/2019 | Soli | G16H 40/20 |
| 2019/0236198 | A1* | 8/2019 | Fernando | G06F 16/27 |
| 2020/0159315 | A1* | 5/2020 | Myers | G06F 9/453 |
| 2020/0159550 | A1* | 5/2020 | Myers | G06F 11/3688 |
| 2020/0159651 | A1* | 5/2020 | Myers | G06F 11/3696 |
| 2020/0346806 | A1* | 11/2020 | Joplin | B65B 57/14 |
| 2020/0402627 | A1* | 12/2020 | Rosomoff | G16H 20/10 |
| 2021/0133085 | A1* | 5/2021 | Myers | G06F 11/3698 |
| 2021/0158907 | A1* | 5/2021 | Sragow | G16H 10/60 |
| 2021/0158916 | A1* | 5/2021 | Sragow | G16H 15/00 |
| 2021/0166795 | A1* | 6/2021 | Sragow | G16H 10/60 |
| 2021/0255880 | A1* | 8/2021 | Markson | G06F 17/11 |
| 2021/0327550 | A1* | 10/2021 | Sragow | G06F 16/355 |
| 2025/0095811 | A1* | 3/2025 | Pait | G16Z 99/00 |

* cited by examiner

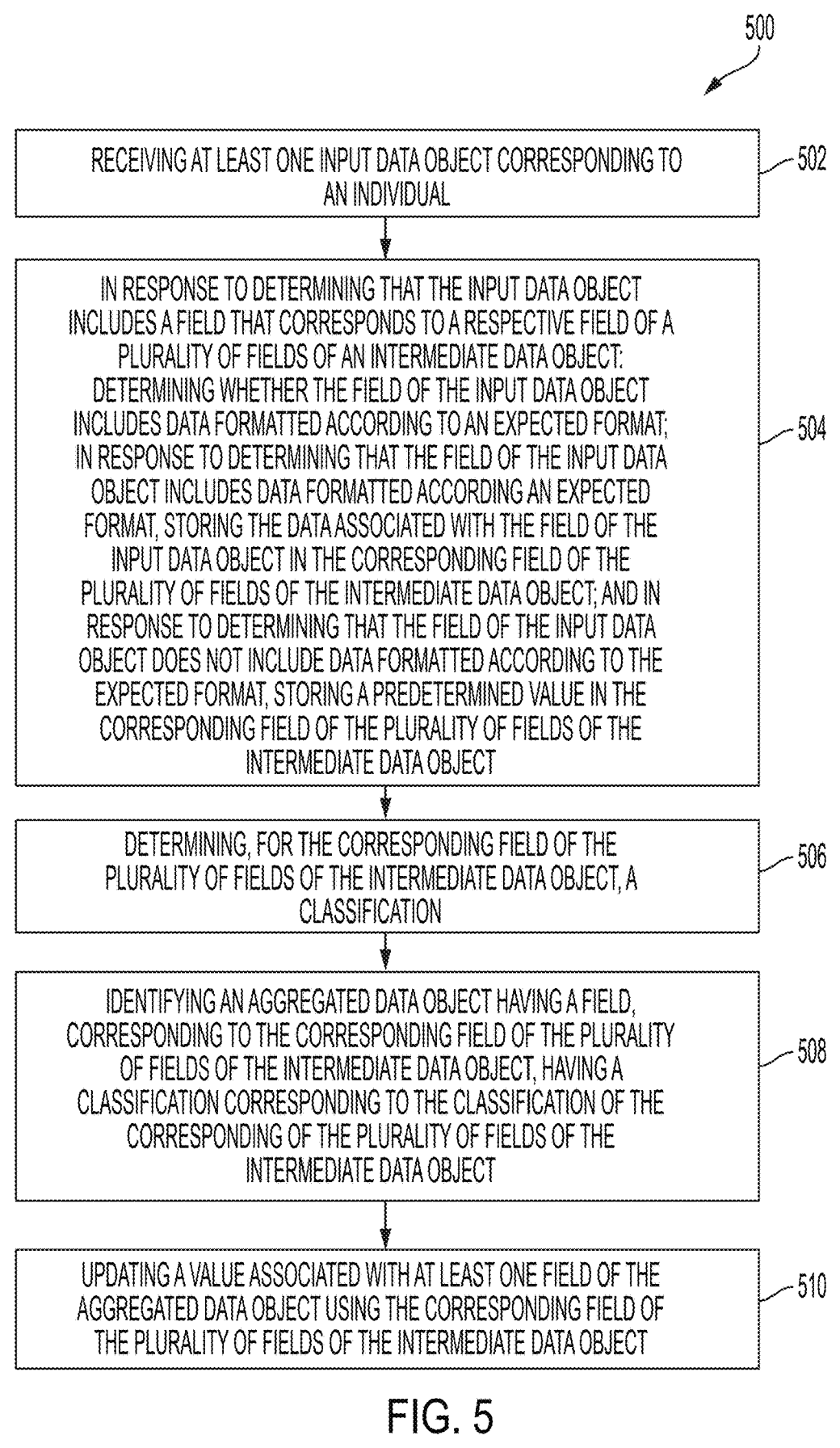

500

RECEIVING AT LEAST ONE INPUT DATA OBJECT CORRESPONDING TO AN INDIVIDUAL — 502

IN RESPONSE TO DETERMINING THAT THE INPUT DATA OBJECT INCLUDES A FIELD THAT CORRESPONDS TO A RESPECTIVE FIELD OF A PLURALITY OF FIELDS OF AN INTERMEDIATE DATA OBJECT: DETERMINING WHETHER THE FIELD OF THE INPUT DATA OBJECT INCLUDES DATA FORMATTED ACCORDING TO AN EXPECTED FORMAT; IN RESPONSE TO DETERMINING THAT THE FIELD OF THE INPUT DATA OBJECT INCLUDES DATA FORMATTED ACCORDING AN EXPECTED FORMAT, STORING THE DATA ASSOCIATED WITH THE FIELD OF THE INPUT DATA OBJECT IN THE CORRESPONDING FIELD OF THE PLURALITY OF FIELDS OF THE INTERMEDIATE DATA OBJECT; AND IN RESPONSE TO DETERMINING THAT THE FIELD OF THE INPUT DATA OBJECT DOES NOT INCLUDE DATA FORMATTED ACCORDING TO THE EXPECTED FORMAT, STORING A PREDETERMINED VALUE IN THE CORRESPONDING FIELD OF THE PLURALITY OF FIELDS OF THE INTERMEDIATE DATA OBJECT — 504

DETERMINING, FOR THE CORRESPONDING FIELD OF THE PLURALITY OF FIELDS OF THE INTERMEDIATE DATA OBJECT, A CLASSIFICATION — 506

IDENTIFYING AN AGGREGATED DATA OBJECT HAVING A FIELD, CORRESPONDING TO THE CORRESPONDING FIELD OF THE PLURALITY OF FIELDS OF THE INTERMEDIATE DATA OBJECT, HAVING A CLASSIFICATION CORRESPONDING TO THE CLASSIFICATION OF THE CORRESPONDING OF THE PLURALITY OF FIELDS OF THE INTERMEDIATE DATA OBJECT — 508

UPDATING A VALUE ASSOCIATED WITH AT LEAST ONE FIELD OF THE AGGREGATED DATA OBJECT USING THE CORRESPONDING FIELD OF THE PLURALITY OF FIELDS OF THE INTERMEDIATE DATA OBJECT — 510

FIG. 5

SYSTEM AND METHOD FOR GENERATING PERSONA DATA OBJECTS USING BIG DATA ANALYTICS

TECHNICAL FIELD

This disclosure relates to data object management, and in particular to systems and methods for generating persona data objects using big data analytics.

BACKGROUND

Medications, such as prescription medications, over-the-counter medications, vitamins, supplements, and the like, are increasingly being delivered by a medication provider, such as a large volume pharmacy and the like, to a residence or other location of an individual requiring such medications. Medications may be delivered using a variety of delivery services, such as a postal service, a parcel delivery service, a contractor, or other service under direct control of a corresponding medication provider, and the like. Further, patients or recipients receiving such medications may be insured by an insurance provider, which may help to offset at least some costs of the medications.

As healthcare professionals continue to prescribe such medications to patients, and as patients continue to use insurance to obtain the mediations, vast amounts of information is generated associated with the prescriptions (e.g., the type of medication prescribed, the dosing guidelines associated with the prescription, the treatment purpose for the medication, and the like), the insurance policy or documents used to obtain the prescriptions, the patient, the healthcare professional associated with the prescription, and the like. This may be referred to as big data and may be useful in identifying trends, averages, and the like.

SUMMARY

This disclosure relates generally to persona data objects.

An aspect of the disclosed embodiments includes a system for providing an aggregated data object. The system includes a processor and a memory. The memory includes instructions that, when executed by the processor, cause the processor to: receive at least one input data object corresponding to an individual, in response to determining that the input data object includes a field that corresponds to a respective field of a plurality of fields of an intermediate data object: determine whether the field of the input data object includes data formatted according to an expected format; in response to determining that the field of the input data object includes data formatted according an expected format, store the data associated with the field of the input data object in the corresponding field of the plurality of fields of the intermediate data object; and, in response to determining that the field of the input data object does not include data formatted according to the expected format, store a predetermined value in the corresponding field of the plurality of fields of the intermediate data object; determine, for the corresponding field of the plurality of fields of the intermediate data object, a classification; identify an aggregated data object having a field, corresponding to the corresponding field of the plurality of fields of the intermediate data object, having a classification corresponding to the classification of the corresponding of the plurality of fields of the intermediate data object; and update a value associated with at least one field of the aggregated data object using the corresponding field of the plurality of fields of the intermediate data object.

Another aspect of the disclosed embodiments includes a method for providing an aggregated data object. The method includes receiving at least one input data object corresponding to an individual and, in response to determining that the input data object includes a field that corresponds to a respective field of a plurality of fields of an intermediate data object: determining whether the field of the input data object includes data formatted according to an expected format; in response to determining that the field of the input data object includes data formatted according an expected format, storing the data associated with the field of the input data object in the corresponding field of the plurality of fields of the intermediate data object; and, in response to determining that the field of the input data object does not include data formatted according to the expected format, storing a predetermined value in the corresponding field of the plurality of fields of the intermediate data object. The method also includes determining, for the corresponding field of the plurality of fields of the intermediate data object, a classification and identifying an aggregated data object having a field, corresponding to the corresponding field of the plurality of fields of the intermediate data object, having a classification corresponding to the classification of the corresponding of the plurality of fields of the intermediate data object. The method also includes updating a value associated with at least one field of the aggregated data object using the corresponding field of the plurality of fields of the intermediate data object.

Another aspect of the disclosed embodiments includes a system for providing an aggregated data object. The system includes a processor and a memory. The memory includes instructions that, when executed by the processor, cause the processor to: receive, from a remote computing device, a plurality of input data objects corresponding to respective individuals; in response to determining that a first input data object includes a field that corresponds to a respective field of a plurality of fields of an intermediate data object: determine whether the field of the first input data object includes data formatted according to an expected format; in response to determining that the field of the first input data object includes data formatted according an expected format, store the data associated with the field of the first input data object in the corresponding field of the plurality of fields of the intermediate data object; and in response to determining that the field of the first input data object does not include data formatted according to the expected format, store a predetermined value in the corresponding field of the plurality of fields of the intermediate data object; determine a respective classification for each field of a subset of fields of the plurality of fields of the intermediate data object; identify an aggregated data object that includes fields having classifications corresponding to at least some of the respective classifications of each field of the subset of fields of the plurality of fields of the intermediate data object; and update a value associated with at least one field of the aggregated data object using a corresponding field of the plurality of fields of the intermediate data object.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 5 is a flow diagram generally illustrating an aggregated data object generation method according to the principles of the present disclosure.

DETAILED DESCRIPTION

Figure 1A:
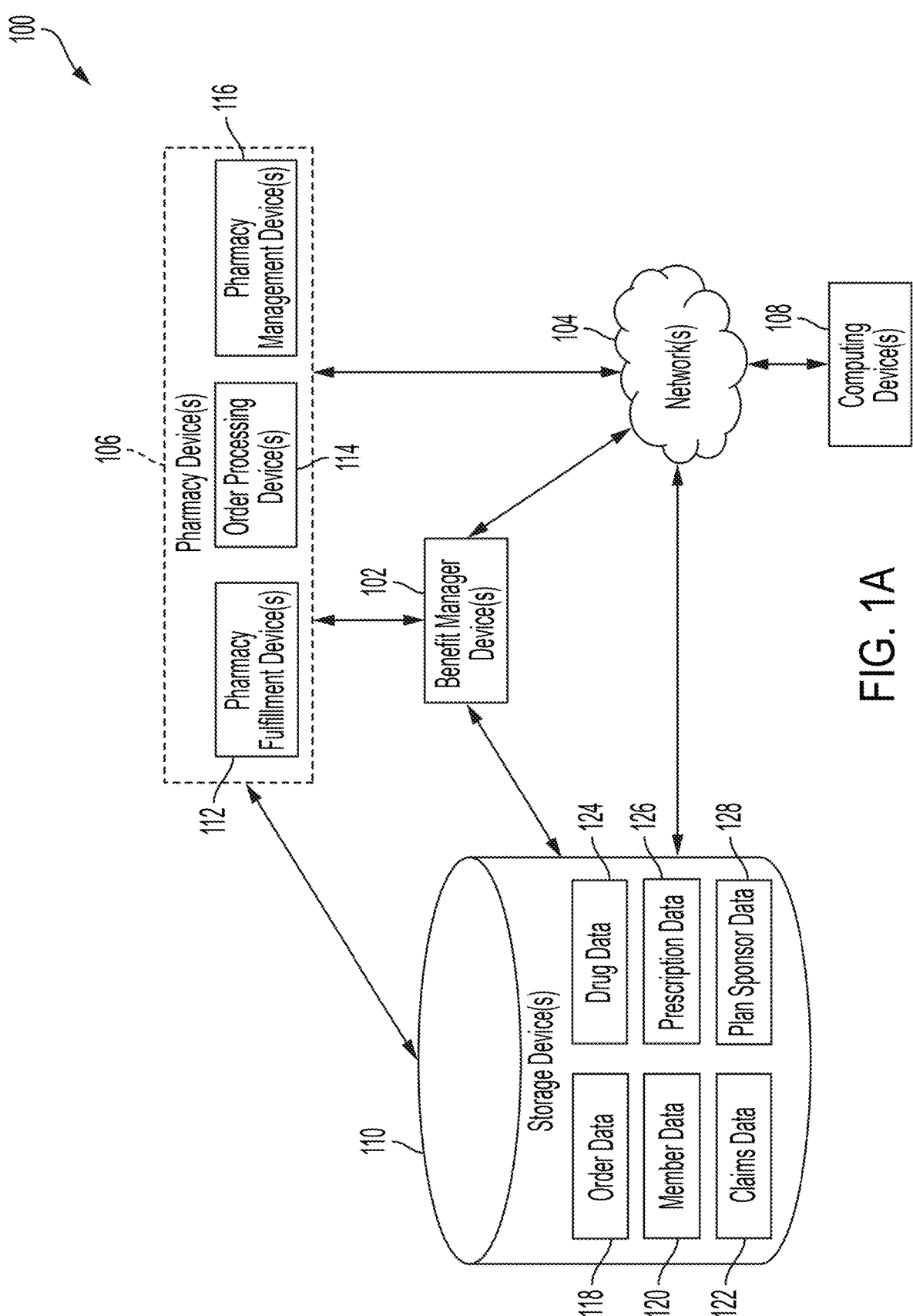
FIG. 1A generally illustrates a functional block diagram of a system including a high-volume pharmacy according to the principles of the present disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, medications, such as prescription medications, over-the-counter medications, vitamins, supplements, and the like, are increasingly being delivered by a medication provider, such as a large volume pharmacy and the like, to a residence or other location of an individual requiring such medications. Medications may be delivered using a variety of delivery services, such as a postal service, a parcel delivery service, a contractor, or other service under direct control of a corresponding medication provider, and the like. Further, patients or recipients receiving such medications may be insured by an insurance provider, which may help to offset at least some costs of the medications.

As healthcare professionals continue to prescribe such medications to patients, and as patients continue to use insurance to obtain the mediations, vast amounts of information is generated associated with the prescriptions (e.g., the type of medication prescribed, the dosing guidelines associated with the prescription, the treatment purpose for the medication, and the like), the insurance policy or documents used to obtain the prescriptions, the patient, the healthcare professional associated with the prescription, and the like. This may be referred to as big data.

Such big data may include data associated with social media platforms associated with the patient, medical record data associated with the patient, census data, prescription metric data, healthcare professional data, and the like. Typically, a user (e.g., such as a healthcare professional, insurance adjuster, insurance actuary, pharmacist, research analyst, and the like), of such data, may collect and analyze the data to identify trends, averages, statistical variances, probabilities, and the like for any number of suitable applications. Such applications may include marketing research, insurance actuarial research, community health research, population health research, scholarly research, and the like.

As the amount of data and/or information available for such applications continues to increase (e.g., in some cases exponentially), the user of such data may move away from characteristics of the individuals (e.g., patients or other suitable individuals) that comprise the data. Accordingly, systems and methods, such as those described herein, configured to provide aggregated data objects (e.g., which may be referred to herein as personas, persona data objects, persona reports, persona output, and the like) that indicate an aggregation of various big data while preserving various aspects of individual or personal characteristic data, may be desirable.

In some embodiments, the systems and methods described herein may be configured to receive at least one input data object corresponding to an individual. The systems and methods described herein may be configured to, in response to determining that the input data object includes a field that corresponds to a respective field of a plurality of fields of an intermediate data object: determine whether the field of the input data object includes data formatted according to an expected format; in response to determining that the field of the input data object includes data formatted according an expected format, store the data associated with the field of the input data object in the corresponding field of the plurality of fields of the intermediate data object; and, in response to determining that the field of the input data object does not include data formatted according to the expected format, store a predetermined value in the corresponding field of the plurality of fields of the intermediate data object.

The systems and methods described herein may be configured to determine, for the corresponding field of the plurality of fields of the intermediate data object, a classification. The systems and methods described herein may be configured to identify an aggregated data object having a field, corresponding to the corresponding field of the plurality of fields of the intermediate data object, having a classification corresponding to the classification of the corresponding of the plurality of fields of the intermediate data object. The systems and methods described herein may be configured to update a value associated with at least one field of the aggregated data object using the corresponding field of the plurality of fields of the intermediate data object.

FIG. 1A is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
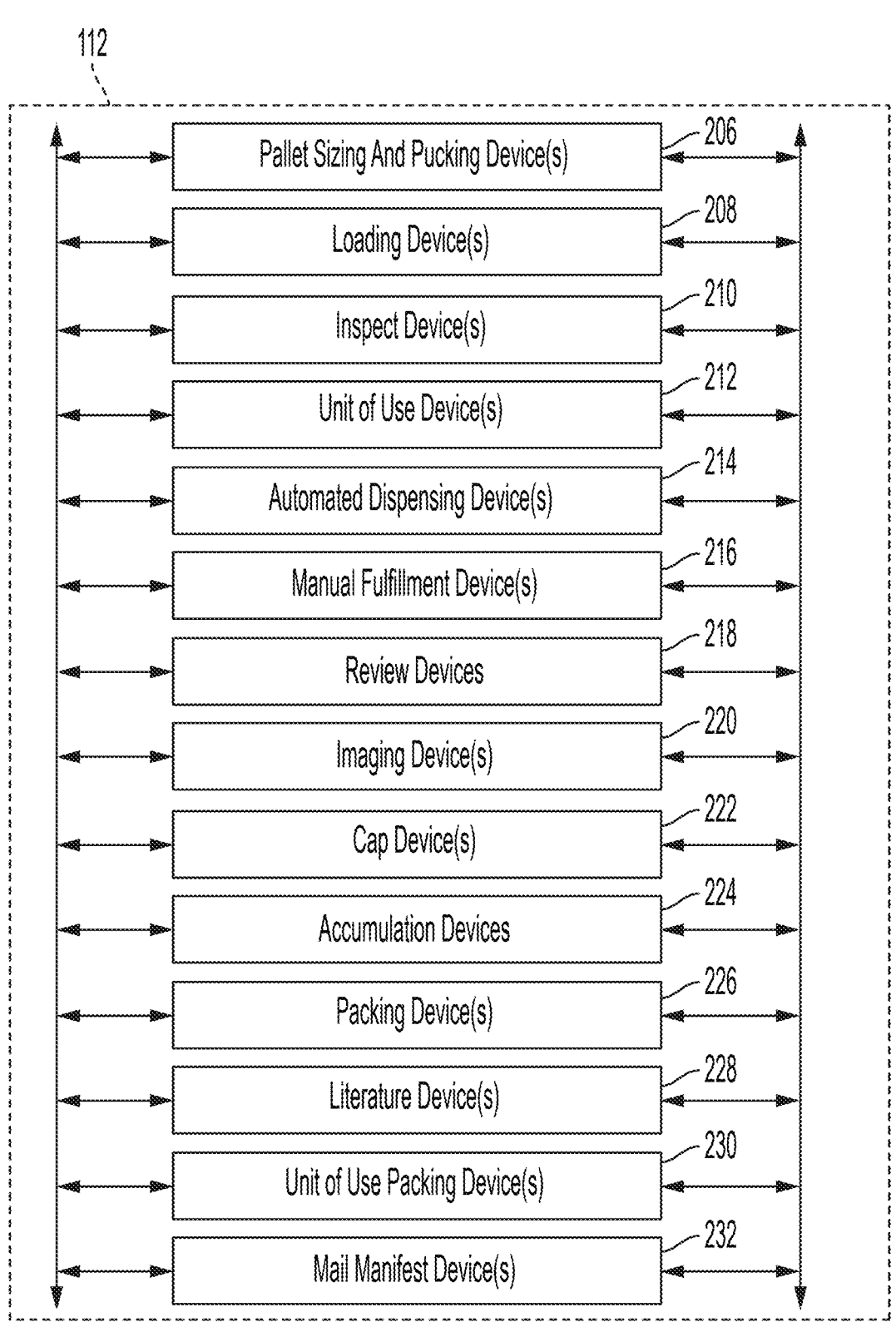
FIG. 2 generally illustrates a functional block diagram of a pharmacy fulfillment device, which may be deployed within the system of FIG. 1A.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
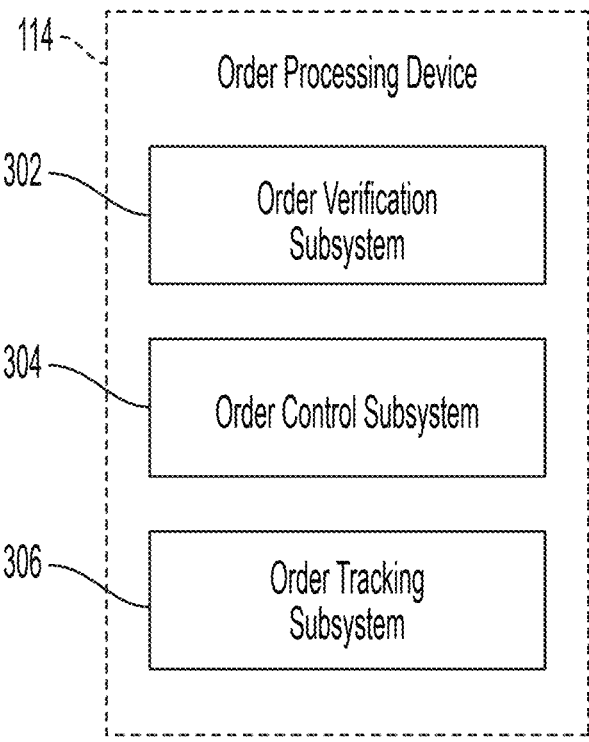
FIG. 3 generally illustrates a functional block diagram of an order processing device, which may be deployed within the system of FIG. 1A.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, and the like. The order tracking subsystem 306 may store data locally (for example, in a memory) or as a portion of the order data 118 stored in the storage device 110.

Figure 1B:
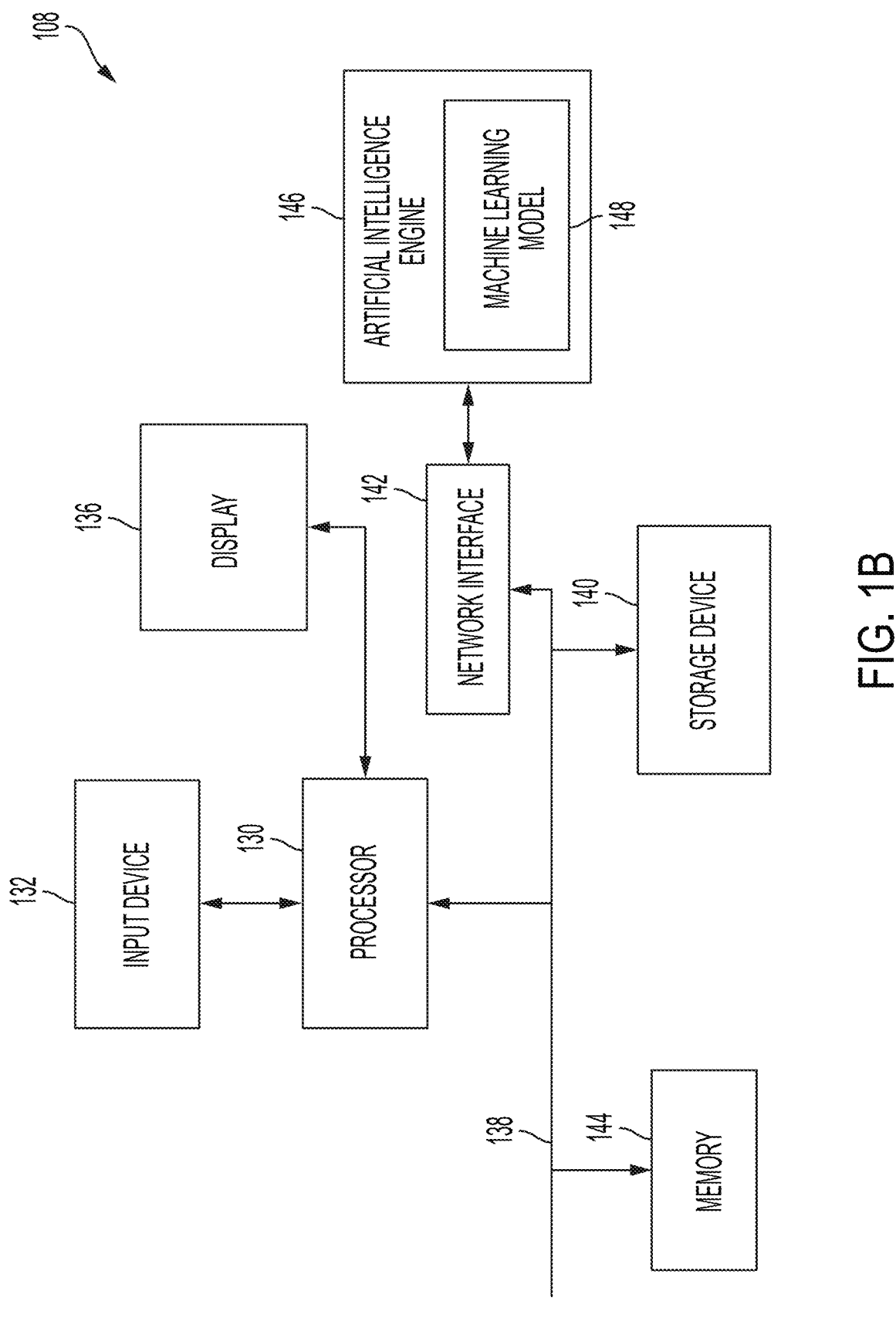
FIG. 1B generally illustrates a computing device according to the principles of the present disclosure.

In some embodiments, the system 100 may include one or more computing devices 108, as is generally illustrated in FIG. 1B. The computing device 108 may include any suitable computing device, such as a mobile computing device, a desktop computing device, a laptop computing device, a server computing device, other suitable computing device, or a combination thereof. The computing device 108 may be used by a user accessing the pharmacy associated with the system 100, as described. Additionally, or alternatively, the computing device 108 may be configured to identify an optimum or substantially optimum combination of data objects, as described.

The computing device 108 may include a processor 130 configured to control the overall operation of computing device 108. The processor 130 may include any suitable processor, such as those described herein. The computing device 108 may also include a user input device 132 that is configured to receive input from a user of the computing device 108 and to communicate signals representing the input received from the user to the processor 130. For example, the user input device 132 may include a button, keypad, dial, touch screen, audio input interface, visual/image capture input interface, input in the form of sensor data, etc.

The computing device 108 may include a display 136 that may be controlled by the processor 130 to display information to the user. A data bus 138 may be configured to facilitate data transfer between, at least, a storage device 140 and the processor 130. The computing device 108 may also include a network interface 142 configured to couple or connect the computing device 108 to various other computing devices or network devices via a network connection, such as a wired or wireless connection, such as the network

104. In some embodiments, the network interface 142 includes a wireless transceiver.

The storage device 140 may include a single disk or a plurality of disks (e.g., hard drives), one or more solid-state drives, one or more hybrid hard drives, and the like. The storage device 140 may include a storage management module that manages one or more partitions within the storage device 140. In some embodiments, storage device 140 may include flash memory, semiconductor (solid state) memory or the like. The computing device 108 may also include a memory 144. The memory 144 may include Random Access Memory (RAM), a Read-Only Memory (ROM), or a combination thereof. The memory 144 may store programs, utilities, or processes to be executed in by the processor 130. The memory 144 may provide volatile data storage, and stores instructions related to the operation of the computing device 108.

In some embodiments, the processor 130 may be configured to execute instructions stored on the memory 144 to, at least, perform the systems and methods described herein. For example, the processor 130 may be configured to generate aggregated data objects, as described. The aggregated data objects may include or be used to model an individual representing a group of individuals, such as a patient or other suitable individual, as described herein (modeling generates a file for a single fictional individual). Additionally, or alternatively, the aggregated data objects may include or be used to model a manufacturer (e.g., such as a drug manufacturer or other suitable manufacturer) representing a group of manufacturers and using data corresponding to various aspects of the manufacturer. Additionally, or alternatively, the aggregated data objects may include or be used to model a physician representing a group of physicians, a pharmacy representing a group of pharmacies, and the like. It should be understood that the aggregated data objects may include or be used to model any suitable individual, business, industry, and the like, in addition to or instead of those described herein. It should be further understood that the aggregated data objects may include data corresponding to any suitable data in addition to or instead of those described herein. An aggregated data object having a field corresponding to the respective field of the intermediate data object and having a classification corresponding to the classification of the respective field of the intermediate data object can be identified. The aggregated data object models a single fictional entity representing a group of entities based on an aggregation of data associated with each entity of the group of entities. The single fictional entity includes a single fictional individual representing the group of entities, and wherein the group of entities includes a group of non-fictional individuals.

Figure 4:
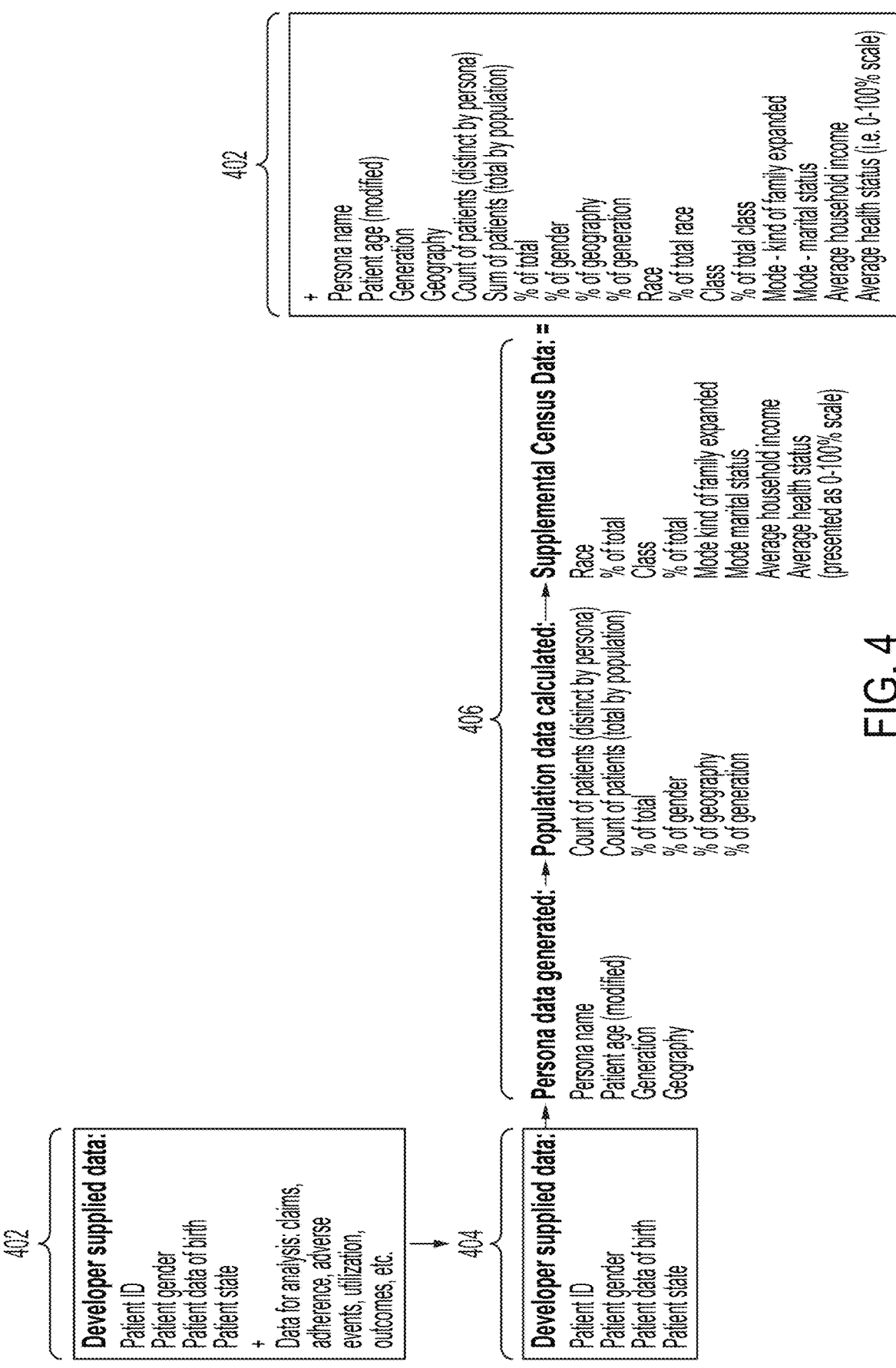
FIG. 4 generally illustrates aggregated data object generation data flow according to the principles of the present disclosure.

In some embodiments, the processor 130 may receive at least one input data object, such as the input data object 402, as is generally illustrated in FIG. 4, corresponding to an individual. The individual may include a patient (e.g., an individual being or having been treated by one or more responsible healthcare professionals, such as one or more of a doctor, dentist, nurse practitioner, nurse, physical therapist, psychologist, psychiatrist, chiropractor, and any other suitable healthcare professional), an insurance policy member (e.g., an individual having an insurance policy through a suitable insurance provider, who may or may have been treated by a responsible healthcare professional), or any other suitable individual. In some embodiments, the individual may include a patient who is also an insurance policy member. It should be understood that, while pharmacies, insurance providers, healthcare professionals, healthcare services, and individuals related so the same are described herein, the principles of the present disclosure may be applied to any suitable data associated with any suitable industry or application. It should be further understood that the processor 130 may receive a plurality of input data objects in addition to or instead of the input data object 402.

The input data object 402 may include a data file, a database table, one or more database entries, a data record (e.g., such as an electronic medical record or other suitable medical record or data record), other suitable data object, or a combination thereof. The input data object 402 may be received from a remotely located computing device, such as a remotely located server, a cloud computing device, a data center computing device, or there suitable computing device. Additionally, or alternatively, the input data object 402 may be stored on or received from a local computing device. In some embodiments, the input data object 402 may correspond to input provided at a graphical user interface by a developer, a user, a healthcare professional, or other suitable individual or entity. In some embodiments, the input data object 402 may correspond to the member data 120.

The input data object 402 may include a plurality of fields having data (e.g., which may include information, values, text strings, and the like) stored in at least some of fields of the plurality of fields. As is generally illustrated in FIG. 4, the input data object 402 may include fields corresponding to a patient identification (ID), a patient gender, a patient data of birth, a patient geographic location (e.g., such as a state, country, region, and the like), data for analysis, other suitable data, or a computation thereof. The data for analysis may include data associated with insurance claims, patient treatment adherence, adverse events associated with the patient or treatment, patient utilization, treatment outcomes, and/or other suitable data. It should be understood that the input data object may include any suitable number of fields in addition to or other than those described herein.

In some embodiments, the processor 130 may determine whether the input data object 402 includes fields that correspond to fields of an intermediate data object, such as the intermediate data object 404. The intermediate data object 404 may include any suitable data object and may be stored in memory associated with the processor 130 (e.g., on the computing device 108 or other suitable location), or remotely stored on a remotely located computing device. The intermediate data object 404 may include fields that correspond to fields of the input data object 402.

In some embodiments, the processor 130 may, in response to determining that the input data object 402 includes a field that corresponds to a respective field of a plurality of fields of the intermediate data object 404, determine whether the field of the input data object 402 includes data formatted according to an expected format. The expected format may be set or correspond to a format of the field of the intermediate data object 404 corresponding to the field of the input data object 402. For example, the expected format for a patient data of birth field of the input data object 402 may include a "mm/dd/yyyy" format. The processor 130 may, in response to determining that the field of the input data object 402 includes data formatted according the expected format, store the data associated with the field of the input data object 402 in the corresponding field of the plurality of fields of the intermediate data object 404. The processor 130 may adjust, change, manipulate, or otherwise alter the data associated with the field of the input data object 402 before storing the data in the corresponding field of the plurality of fields of the intermediate data object 404. For example, the processor 130 may change data indicating a birth date of the patient to a generic month and day, while maintaining the year indicated by the data.

Alternatively, the processor 130 may, in response to determining that the field of the input data object 402 does not include data formatted according to the expected format, store a predetermined value in the corresponding field of the plurality of fields of the intermediate data object 404. The predetermined value includes a null value or other suitable value. The processor 130 may continue, as described, for other fields of the input data object 402. The processor 130 may store the intermediate data object 404 in a corresponding memory or in a remote location (e.g., on a remotely located computing device or other suitable location).

In some embodiments, the processor 130 may determine, for at least some fields of the plurality of fields of the intermediate data object 404, a corresponding classification. For example, the processor 130 may determine a classification for the patient date of birth. The classification may indicate a generation (e.g., such as "baby boomer," "generation X," "millennial," and the like) based on the birth data of the patient stored in the corresponding field of the intermediate data object 404.

In some embodiments, the processor 130 may identify a plurality of aggregated data objects, including the aggregated data object 406, having a field having the same classification as the classified field of the intermediate data object 404. For example, the processor 130 may identify all aggregated data objects having a generation field having the same classification as the patient data of birth field of the intermediate data object 404. The aggregated data objects, including the aggregated data object 406, may include any suitable data object, such as those described herein. The aggregated data object 406 and a plurality of other aggregated data objects may be stored in a memory of the computing device 108 or stored in a remotely located computing device.

Each aggregated data object, such as the aggregated data object 406, may include a plurality of persona data generated fields, including, but not limited to, a persona name field (e.g., a name assigned to the corresponding aggregated data object to simulate a human persona), a patient age field (e.g., corresponding to a generation of the aggregated data object and/or an average age of patients corresponding to the aggregated data object), a generation field (e.g., indicating a generation classification), a gender field (e.g., indicating a gender classification), a geography field (e.g., indicating a geography classification), other suitable fields, or a combination thereof.

Additionally, or alternatively, each aggregated data object, such as the aggregated data object 406, may include a plurality of population data calculation fields, including, but not limited to, a count of patients (distinct by persona) field (e.g., indicating a number of patients that correspond to the persona of the aggregated data object 406), a count of patients (total by population) field (e.g., indicating a count of all patients for a given population, which may be defined for the aggregated data object 406), a % of total field (e.g., indicating the percentage total of the count of patients for the persona relative to the count of patients for the population), a % of gender field (e.g., indicating a percentage of the persona gender relative to the population), a % of geography field (e.g., indicating a percentage of the persona geography relative to the population), a % of generation field (e.g., indicating a percentage of the persona generation relative to the population), other suitable fields, or a combination thereof.

Additionally, or alternatively, each aggregated data object, such as the aggregated data object 406, may include a plurality of supplemental census data fields, including, but not limited to, a race % of total field (e.g., indicating one or more percentages of races comprising the population), a class % of total field (e.g., indicating a percentage of one or more socioeconomic classes comprising the population), a mode kind of family extended field (e.g., indicating a statistical mode of the type of family of the population), a mode marital status field (e.g., indicating a statistical mode of the marital status of the population), an average household income field (e.g., indicating an average household income for the population), an average health status (presented as a 0-100% scale or other suitable scale) field (e.g., indicating an average health status of the population), other suitable fields, or a combination thereof. In some embodiments, the processor 130 may receive or retrieve government census data and/or private census data from a remotely located computing device.

The processor 130 may identify aggregated data objects (e.g., of the aggregated data objects, including the aggregated data object 406, having the same generation classification of the intermediate data object 404) having a field indicating a gender corresponding to the gender indicated by the patient gender field of the intermediate data object 404. The processor 130 may then identify aggregated data objects (e.g., of the aggregated data objects, including the aggregated data object 406, having the same generation classicization and the same gender classification as the intermediate data object 404) having a geographic location (e.g., indicated by a geography field) corresponding to a patient geography indicated by a corresponding field of the intermediate data object 404.

If the processor 130 does not identify an aggregated data object having a generation classification, a gender classification, and a geography classification corresponding to the intermediate data object 404, the processor 130 may generate a new aggregated data object. Alternatively, if the processor 130 identifies an aggregated data object, such as the aggregated data object 406, having a generation classification, a gender classification, and a geography classification corresponding to the intermediate data object 404, the processor 130 may update various fields of the population data calculated fields of the aggregated data object 406. For example, the processor 130 may, based on the data of fields of the intermediate data object 404, update the count of patients field (e.g., by incrementing the count of patients field), update the % of total field (e.g., by calculating a revised value), update the % of gender field (e.g., by calculating a revised value), update the % of gender field (e.g., by calculating a revised value), update % of geography field (e.g., by calculating a revised value), update the % of generation field (e.g., by calculating a revised value), and/or update other suable fields of the aggregated data object 406.

In some embodiments, the processor 130 generate an output 408. The output may include the aggregated data object 406. The processor 130 may provide at a display, such as the display 136, the output 408. In some embodiments, the processor 130 may identify one or more images stored on the computing device 108 or on a remotely located computing device corresponding to the persona of the aggregated data object 406. The one or more images may include an image of a persona corresponding to the persona name of the aggregated data object 406, a map corresponding to the persona geography of the aggregated data object 406, or other suitable images. The processor 130 may include, with the output 408, the one or more images. Additionally, or alternatively, the processor 130 may generate one or more graphical representations of the various fields of the aggregated data object 406. For example, the processor 130 may generate one or more graphical representations of the persona data generated fields, of the population data calculated fields, and/or of the supplemental censes data fields of the aggregated data object 406. The processor 130 may include the one or more graphical representations with the output 408. It should be understood that the processor 130 may generate any suitable number of aggregated data objects and/or update any suitable number of aggregated data objects, based on a plurality of input data objects.

In some embodiments, the computing device 108 and/or the system 100 may perform the methods described herein. However, the methods described herein as performed by the computing device 108 and/or the system 100 are not meant to be limiting, and any type of software executed on a computing device or a combination of various computing devices can perform the methods described herein without departing from the scope of this disclosure.

FIG. 5 is a flow diagram generally illustrating an aggregated data object generation method 500 according to the principles of the present disclosure. At 502, the method 500 receives at least one input data object corresponding to an individual. For example, the processor 130 may receive the input data object 402.

At 504, the method 500, in response to determining that the input data object includes a field that corresponds to a respective field of a plurality of fields of an intermediate data object, determines whether the field of the input data object includes data formatted according to an expected format. For example, the processor 130 may determine whether the field of the input data object 402 includes data formatted according to an expected format. The method 500 may, in response to determining that the field of the input data object includes data formatted according an expected format, store the data associated with the field of the input data object in the corresponding field of the plurality of fields of the intermediate data object 404. For example, the processor 130 may, in response to determining that the field of the input data object 402 includes data formatted according an expected format, store the data associated with the field of the input data object 402 in the corresponding field of the plurality of fields of the intermediate data object 404. The method 500 may, in response to determining that the field of the input data object does not include data formatted according to the expected format, store a predetermined value in the corresponding field of the plurality of fields of the intermediate data object 404. For example, the processor 130 may, in response to determining that the field of the input data object 402 does not include data formatted according to the expected format, store a predetermined value in the corresponding field of the plurality of fields of the intermediate data object 404.

At 506, the method 500 determines, for the corresponding field of the plurality of fields of the intermediate data object, a classification. For example, the processor 130 may determine, for the corresponding field of the plurality of fields of the intermediate data object 404, the classification.

At 508, the method 500 identifies an aggregated data object having a field, corresponding to the corresponding field of the plurality of fields of the intermediate data object, having a classification corresponding to the classification of the corresponding of the plurality of fields of the intermediate data object. For example, the processor 130 may identify the aggregated data object 406 based on the classification of the field of the plurality of fields of the intermediate data object 404.

At 510, the method 500 updates a value associated with at least one field of the aggregated data object using the corresponding field of the plurality of fields of the intermediate data object. For example, the processor 130 may update the value associated with at least one field of the aggregated data object 406 using the corresponding field of the plurality of fields of the intermediate data object 404.

In some embodiments, a system for providing an aggregated data object includes a processor and a memory. The memory includes instructions that, when executed by the processor, cause the processor to: receive at least one input data object corresponding to an individual, in response to determining that the input data object includes a field that corresponds to a respective field of a plurality of fields of an intermediate data object: determine whether the field of the input data object includes data formatted according to an expected format; in response to determining that the field of the input data object includes data formatted according an expected format, store the data associated with the field of the input data object in the corresponding field of the plurality of fields of the intermediate data object; and, in response to determining that the field of the input data object does not include data formatted according to the expected format, store a predetermined value in the corresponding field of the plurality of fields of the intermediate data object; determine, for the corresponding field of the plurality of fields of the intermediate data object, a classification; identify an aggregated data object having a field, corresponding to the corresponding field of the plurality of fields of the intermediate data object, having a classification corresponding to the classification of the corresponding of the plurality of fields of the intermediate data object; and update a value associated with at least one field of the aggregated data object using the corresponding field of the plurality of fields of the intermediate data object.

In some embodiments, the predetermined value includes a null value. In some embodiments, the classification includes a generational indicator. In some embodiments, the classification includes a gender indicator. In some embodiments, the classification includes a geographic indicator. In some embodiments, the instructions further cause the processor to update the value associated with the at least one field of the aggregated data object using the corresponding field of the plurality of fields of the intermediate data object by incrementing the value associated with the at least one field of the aggregated data object in response to determining that the corresponding field of the plurality of fields of the intermediate data object does not include the predetermined value. In some embodiments, the instructions further cause the processor to update the value associated with the at least one field of the aggregated data object using the corresponding field of the plurality of fields of the intermediate data object by calculating a percentage associated with the value associated with the at least one field of the aggregated data object based using a value associated with the corresponding field of the plurality of fields of the intermediate data object in response to determining that the corresponding field of the plurality of fields of the intermediate data object does not include the predetermined value. In some embodiments, the instructions further cause the processor to update the value associated with the at least one field of the aggregated data object using the corresponding field of the plurality of fields of the intermediate data object by calculating an average associated with the value associated with the at least one field of the aggregated data object based using a value associated with the corresponding field of the plurality of fields of the intermediate data object in response to determining that the corresponding field of the plurality of fields of the intermediate data object does not include the predetermined value. In some embodiments, the instructions further cause the processor to provide, at a display, a graphical user interface that includes at least the aggregated data object.

In some embodiments, a method for providing an aggregated data object includes receiving at least one input data object corresponding to an individual and, in response to determining that the input data object includes a field that corresponds to a respective field of a plurality of fields of an intermediate data object: determining whether the field of the input data object includes data formatted according to an expected format; in response to determining that the field of the input data object includes data formatted according an expected format, storing the data associated with the field of the input data object in the corresponding field of the plurality of fields of the intermediate data object; and, in response to determining that the field of the input data object does not include data formatted according to the expected format, storing a predetermined value in the corresponding field of the plurality of fields of the intermediate data object. The method also includes determining, for the corresponding field of the plurality of fields of the intermediate data object, a classification and identifying an aggregated data object having a field, corresponding to the corresponding field of the plurality of fields of the intermediate data object, having a classification corresponding to the classification of the corresponding of the plurality of fields of the intermediate data object. The method also includes updating a value associated with at least one field of the aggregated data object using the corresponding field of the plurality of fields of the intermediate data object.

In some embodiments, the predetermined value includes a null value. In some embodiments, the classification includes a generational indicator. In some embodiments, the classification includes a gender indicator. In some embodiments, the classification includes a geographic indicator. In some embodiments, updating the value associated with the at least one field of the aggregated data object using the corresponding field of the plurality of fields of the intermediate data object includes incrementing the value associated with the at least one field of the aggregated data object in response to determining that the corresponding field of the plurality of fields of the intermediate data object does not include the predetermined value. In some embodiments, updating the value associated with the at least one field of the aggregated data object using the corresponding field of the plurality of fields of the intermediate data object includes calculating a percentage associated with the value associated with the at least one field of the aggregated data object based using a value associated with the corresponding field of the plurality of fields of the intermediate data object in response to determining that the corresponding field of the plurality of fields of the intermediate data object does not include the predetermined value. In some embodiments, updating the value associated with the at least one field of the aggregated data object using the corresponding field of the plurality of fields of the intermediate data object includes calculating an average associated with the value associated with the at least one field of the aggregated data object based using a value associated with the corresponding field of the plurality of fields of the intermediate data object in response to determining that the corresponding field of the plurality of fields of the intermediate data object does not include the predetermined value. In some embodiments, the method also includes providing, at a display, a graphical user interface that includes at least the aggregated data object.

In some embodiments, a system for providing an aggregated data object includes a processor and a memory. The memory includes instructions that, when executed by the processor, cause the processor to: receive, from a remote computing device, a plurality of input data objects corresponding to respective individuals; in response to determining that a first input data object includes a field that corresponds to a respective field of a plurality of fields of an intermediate data object: determine whether the field of the first input data object includes data formatted according to an expected format; in response to determining that the field of the first input data object includes data formatted according an expected format, store the data associated with the field of the first input data object in the corresponding field of the plurality of fields of the intermediate data object; and in response to determining that the field of the first input data object does not include data formatted according to the expected format, store a predetermined value in the corresponding field of the plurality of fields of the intermediate data object; determine a respective classification for each field of a subset of fields of the plurality of fields of the intermediate data object; identify an aggregated data object that includes fields having classifications corresponding to at least some of the respective classifications of each field of the subset of fields of the plurality of fields of the intermediate data object; and update a value associated with at least one field of the aggregated data object using a corresponding field of the plurality of fields of the intermediate data object.

In some embodiments, the instructions further cause the processor to provide, at a display, a graphical user interface that includes at least the aggregated data object.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Implementations of the systems, algorithms, methods, instructions, etc., described herein may be realized in hardware, software, or any combination thereof. The hardware may include, for example, computers, intellectual property (IP) cores, application-specific integrated circuits (ASICs), programmable logic arrays, optical processors, program-mable logic controllers, microcode, microcontrollers, serv-ers, microprocessors, digital signal processors, or any other suitable circuit. In the claims, the term "processor" should be understood as encompassing any of the foregoing hard-ware, either singly or in combination. The terms "signal" and "data" are used interchangeably.

What is claimed is:

1. A system for providing an aggregated data object, the system comprising:

a pharmacy fulfilment device associated with pharmacy order fulfilment of a high-volume pharmacy, wherein the pharmacy fulfilment device:

receives, from an order processing device, instructions to fulfill a pharmacy order;

controls at least one robotic arm to position a puck on a pallet;

controls a loading device to load a prescription con-tainer into the puck;

controls at least one dispensing device to fulfill the pharmacy order by dispensing at least one item into the prescription container; and in response to the dispensing device dispensing the at least one item into the prescription container, gen-erates member data associated with pharmacy order;

a processor in communication with the pharmacy fulfil-ment device; and a memory including instructions that, when executed by the processor, cause the processor to:

receive at least one input data object corresponding to an individual, wherein the at least one input data object includes the member data generated by the pharmacy fulfilment device in response to the dis-pensing device dispensing the at least one item into the prescription container;

identify an intermediate data object associated with the at least one input data object; and in response to determining that the input data object includes a field that corresponds to a respective field of the intermediate data object:

determine whether the field of the input data object includes data formatted according to an expected format, wherein the expected format corresponds to a format of the respective field of the interme-diate data object;

in response to determining that the field of the input data object includes data formatted according the expected format, store the data associated with the field of the input data object in the respective field of the intermediate data object;

in response to determining that the field of the input data object does not include data formatted according to the expected format, store a prede-termined value in the respective field of the inter-mediate data object;

determine, for the respective field of the intermediate data object, a classification;

identify an aggregated data object having a field corresponding to the respective field of the inter-mediate data object, having a classification corre-sponding to the classification of the respective field of the intermediate data object, wherein the aggregated data object models a single fictional entity representing a group of entities based on an aggregation of data associated with each entity of the group of entities, wherein the single fictional entity includes a single fictional individual representing the group of entities, and wherein the group of entities includes a group of non-fictional individuals; and update a value associated with at least one field of the aggregated data object using the respective field of the intermediate data object.

2. The system of claim 1, wherein the predetermined value includes a null value.

3. The system of claim 1, wherein the classification includes a generational indicator.

4. The system of claim 1, wherein the classification includes a gender indicator.

5. The system of claim 1, wherein the classification includes a geographic indicator.

6. The system of claim 1, wherein the instructions further cause the processor to update the value associated with the at least one field of the aggregated data object using the respective field of the intermediate data object by increment-ing the value associated with the at least one field of the aggregated data object in response to determining that the respective field of the intermediate data object does not include the predetermined value.

7. The system of claim 1, wherein the instructions further cause the processor to update the value associated with the at least one field of the aggregated data object using the respective field of the intermediate data object by calculating a percentage associated with the value associated with the at least one field of the aggregated data object using a value associated with the respective field of the intermediate data object in response to determining that the respective field of the intermediate data object does not include the predeter-mined value.

8. The system of claim 1, wherein the instructions further cause the processor to update the value associated with the at least one field of the aggregated data object using the respective field of the intermediate data object by calculating an average associated with the value associated with the at least one field of the aggregated data object using a value associated with the respective field of the intermediate data object in response to determining that the respective field of the intermediate data object does not include the predeter-mined value.

9. The system of claim 1, wherein the instructions further cause the processor to provide, at a display, a graphical user interface that includes at least the aggregated data object.

10. A method for providing an aggregated data object, the method comprising:

receiving, at a pharmacy fulfilment device associated with pharmacy order fulfilment of a high-volume pharmacy and from an order processing device, instructions to fulfill a pharmacy order;

controlling at least one robotic arm to position a puck on a pallet;

controlling a loading device to load a prescription con-tainer into the puck;

controlling at least one dispensing device to fulfill the pharmacy order by dispensing at least one item into the prescription container; and in response to the dispensing device dispensing the at least one item into the prescription container, generat-ing member data associated with pharmacy order;

receiving at least one input data object corresponding to an individual, wherein the at least one input data object includes the member data;

identifying an intermediate data object associated with the at least one input data object; and in response to determining that the input data object includes a field that corresponds to a respective field of the intermediate data object:

determining whether the field of the input data object includes data formatted according to an expected format, wherein the expected format corresponds to a format of the respective field of the intermediate data object;

in response to determining that the field of the input data object includes data formatted according the expected format, storing the data associated with the field of the input data object in the respective field of the intermediate data object;

in response to determining that the field of the input data object does not include data formatted according to the expected format, storing a predetermined value in the respective field of the intermediate data object;

determining, for the respective field of the intermediate data object, a classification;

identifying an aggregated data object having a field corresponding to the respective field of the intermediate data object, having a classification corresponding to the classification of the respective field of the intermediate data object, wherein the aggregated data object models a single fictional entity representing a group of entities based on an aggregation of data associated with each entity of the group of entities, wherein the single fictional entity includes a single fictional individual representing the group of entities, and wherein the group of entities includes a group of non-fictional individuals; and updating a value associated with at least one field of the aggregated data object using the respective field of the intermediate data object.

11. The method of claim 10, wherein the predetermined value includes a null value.

12. The method of claim 10, wherein the classification includes a generational indicator.

13. The method of claim 10, wherein the classification includes a gender indicator.

14. The method of claim 10, wherein the classification includes a geographic indicator.

15. The method of claim 10, wherein updating the value associated with the at least one field of the aggregated data object using the respective field of the intermediate data object includes incrementing the value associated with the at least one field of the aggregated data object in response to determining that the respective field of the intermediate data object does not include the predetermined value.

16. The method of claim 10, wherein updating the value associated with the at least one field of the aggregated data object using the respective field of the intermediate data object includes calculating a percentage associated with the value associated with the at least one field of the aggregated data object using a value associated with the respective field of the intermediate data object in response to determining that the respective field of the intermediate data object does not include the predetermined value.

17. The method of claim 10, wherein updating the value associated with the at least one field of the aggregated data object using the respective field of the intermediate data object includes calculating an average associated with the value associated with the at least one field of the aggregated data object using a value associated with the respective field of the intermediate data object in response to determining that the respective field of the intermediate data object does not include the predetermined value.

18. The method of claim 10, further comprising providing, at a display, a graphical user interface that includes at least the aggregated data object.

19. A system for providing an aggregated data object, the system comprising:

a pharmacy fulfilment device associated with pharmacy order fulfilment of a high-volume pharmacy, wherein the pharmacy fulfilment device:

receives, from an order processing device, instructions to fulfill a pharmacy order;

controls at least one robotic arm to position a puck on a pallet;

controls a loading device to load a prescription container into the puck;

controls at least one dispensing device to fulfill the pharmacy order by dispensing at least one item into the prescription container; and in response to the dispensing device dispensing the at least one item into the prescription container, generates member data associated with pharmacy order;

a processor in communication with the pharmacy fulfilment device; and a memory including instructions that, when executed by the processor, cause the processor to:

receive, from a remote computing device in communication with the pharmacy fulfilment device, a plurality of input data objects corresponding to respective individuals, wherein a first input data object of the plurality of input data objects includes the member data generated by the pharmacy fulfilment device in response to the dispensing device dispensing the at least one item into the prescription container;

identify an intermediate data object associated with the first input data object; and in response to determining that the first input data object includes a field that corresponds to a respective field of the intermediate data object:

determine whether the field of the first input data object includes data formatted according to an expected format, wherein the exacted format corresponds to a format of the respective field of the intermediate data object;

in response to determining that the field of the first input data object includes data formatted according the expected format, store the data associated with the field of the first input data object in the respective field of the intermediate data object;

in response to determining that the field of the first input data object does not include data formatted according to the expected format, store a predetermined value in the respective field of the intermediate data object;

determine a respective classification for each field of a subset of fields of a plurality of fields of the intermediate data object;

identify an aggregated data object that includes fields having classifications corresponding to at least some of the respective classifications of each field of the subset of fields of the plurality of fields of the intermediate data object, wherein the aggregated data object models a single fictional entity representing a group of entities based on an aggregation of data associated with each entity of the group of entities, wherein the single fictional entity includes a single fictional individual representing the group of entities, and wherein the group of entities includes a group of non-fictional individuals; and update a value associated with at least one field of the aggregated data object using at least the respective field of the intermediate data object.

20. The system of claim 19, wherein the instructions further cause the processor to provide, at a display, a graphical user interface that includes at least the aggregated data object.

\* \* \* \* \*